United States Patent
Ae et al.

(10) Patent No.: US 8,921,551 B2
(45) Date of Patent: *Dec. 30, 2014

(54) PROCESS OF A QUATERNARY AMMONIUM SALT

(75) Inventors: Nobuyuki Ae, Osaka (JP); Yuji Fujiwara, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 761 days.

This patent is subject to a terminal disclaimer.

(21) Appl. No.: 13/093,927

(22) Filed: Apr. 26, 2011

(65) Prior Publication Data

US 2011/0263847 A1 Oct. 27, 2011

Related U.S. Application Data

(60) Provisional application No. 61/327,809, filed on Apr. 26, 2010.

(51) Int. Cl.
 *C07D 487/10* (2006.01)
 *C07D 417/04* (2006.01)

(52) U.S. Cl.
 CPC ............ *C07D 487/10* (2013.01); *C07D 417/04* (2013.01)
 USPC ............................... 544/368; 546/16; 546/17

(58) Field of Classification Search
 CPC .. C07D 221/20; C07D 221/22; C07D 275/04; C07D 401/08; C07D 417/14; C07D 471/10; C07D 487/10; C07D 491/107
 USPC ...................................... 544/368; 546/16, 17
 See application file for complete search history.

(56) References Cited

U.S. PATENT DOCUMENTS

| 5,532,372 | A | | 7/1996 | Saji et al. | |
|---|---|---|---|---|---|
| 5,780,632 | A | * | 7/1998 | Saji et al. | ................. 546/15 |
| 8,586,737 | B2 | * | 11/2013 | Ae et al. | ................. 544/231 |

FOREIGN PATENT DOCUMENTS

| EP | 0 464 846 | * | 7/1991 | ........... C07D 417/12 |
|---|---|---|---|---|
| EP | 0464846 | A1 | 1/1992 | |
| JP | 5-017440 | A | 1/1993 | |
| JP | 8-333368 | A | 12/1996 | |
| JP | 2-800953 | B2 | 9/1998 | |
| JP | 2003-160583 | A | 6/2003 | |
| JP | 2006-169154 | * | 6/2006 | ........... C07D 417/12 |
| JP | 2006-169154 | A | 6/2006 | |
| JP | 2006-169155 | * | 6/2006 | ........... C07D 471/10 |
| JP | 2006-169155 | A | 6/2006 | |
| WO | WO 2011/002103 | * | 1/2011 | ........... C07D 209/56 |

OTHER PUBLICATIONS

Stará et al., "Nucleophilic Cleavage of 4,5-Dihydro-3H-dinaphth[2,1-c:1',2'-e]azepinim, Quaternary Salts. A Convenient Approach to New Axially Dissymmetric and Axially Asymmetric Ligands", J. Org. Chem., 1992, vol. 57, No. 25, pp. 6966-6969.
Translation of: JP 8-333368 A (Dec. 17, 1996).
Translation of: JP 2003-160583 A (Jun. 3, 2003).
Translation of: JP 2006-169154 A (Jun. 29, 2006).
Translation of: JP 2006-169155 A (Jun. 29, 2006).
International Preliminary Report on Patentability, dated Oct. 30, 2012, International Application No. PCT/JP2011/060570.
European Patent Office, "Communication of Extended European Search Report," dated , Jan. 16, 2014, Application No. 11775164.4, 6 pp.

* cited by examiner

*Primary Examiner* — Erich A Leeser

(74) *Attorney, Agent, or Firm* — Finnegan, Henderson, Farabow, Garrett & Dunner, L.L.P.

(57) ABSTRACT

The present invention relates to a novel process for preparing quaternary ammonium salt derivatives.

17 Claims, No Drawings

PROCESS OF A QUATERNARY AMMONIUM SALT

CROSS REFERENCE TO RELATED APPLICATION

This application is a utility application and claims the benefit of U.S. Provisional Application No. 61/327,809, filed Apr. 26, 2010 the complete disclosure of which is incorporated herein by reference.

TECHNICAL FIELD

The present invention relates to a process for preparing quaternary ammonium salt derivatives.

BACKGROUND ART

An imide derivative or a salt thereof whose typical example is a compound of formula (8) mentioned later or an acid addition salt thereof is known to be useful as a medicament for treating schizophrenia, senile psychiatric disorder, bipolar disorder, neurosis, etc. (Patent Reference 1). And, some processes for preparing an imide derivative of the following formula (I):

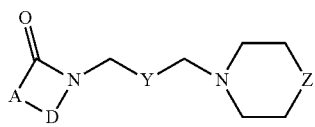
(I)

wherein A is optionally substituted $C_{2-4}$ alkylene group or other, D is carbonyl group or other, Y is optionally substituted $C_{1-2}$ alkylene group, Z is optionally substituted imino group or other
are also reported. For example, Patent Reference 2 discloses a process for preparing the imide derivative of the above-mentioned formula (I) which comprises reacting a compound of formula (II):

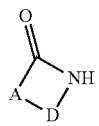
(II)

wherein A is optionally substituted $C_{2-4}$ alkylene group or other, and D is carbonyl group or other, and a quaternary ammonium salt of formula (III):

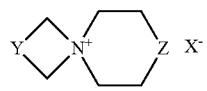
(III)

wherein Y is optionally substituted $C_{1-2}$ alkylene group, Z is optionally substituted imino group or other, $X^-$ is a counter-anion
in the presence of a solid inorganic base and water.

In addition, Patent Reference 3 discloses that the compound of formula (III) can be prepared by reacting a compound of formula (IV):

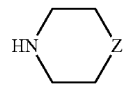
(IV)

wherein Z is optionally substituted imino group or other, and a compound of formula (V):

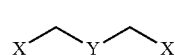
(V)

wherein X is a group which can become the above counter-anion $X^-$ after cleavage, and Y is optionally-substituted $C_{1-2}$ alkylene group in the presence of potassium carbonate whose specific surface area is less than 1.8 $m^2/g$.

Furthermore, Patent Reference 4 discloses a process for preparing the compound of formula (III) which comprises reacting the compound of formula (IV) and the compound of formula (V) in an organic solvent in the presence of potassium carbonate whose mean particle size (50% D) is not more than 200 μm.

However, these processes have some problems on the preparing processes, for example, the product of formula (I) contains a by-product (hereinafter, referred to as "by-product (R)"), or the reaction time of the preparing processes is unstable. Such by-product (R) might cause the quality loss of the imide compound of formula (I), hence it is necessary to remove the by-product through a purification. Thus, it has been desired to further reduce the producing of by-product (R) and stabilize the reaction time from the viewpoint of the yield of the product and the production cost.

PRIOR ART

[Patent Reference]
  [Patent Reference 1] JP 2800953 B
  [Patent Reference 2] JP 2003-160583 A
  [Patent Reference 3] JP 2006-169155 A
  [Patent Reference 4] JP 2006-169154 A

DISCLOSURE OF INVENTION

Problem to be Solved by the Invention

Under the situation, the present inventors have extensively studied to reduce the producing of by-product (R) and then have found that the cause of producing by-product (R) is potassium carbonate which is used in the reaction of compound (IV) and compound (V) as a base. And, the inventors have further extensively studied other bases instead of potassium carbonate which has been understood as an optimal base in the reaction process and then have found that the producing of by-product (R) can be reduced by using an excessive amount of the following compound of formula (3) instead of potassium carbonate in the reaction of the following compound of formula (1) and the compound of formula (3), and the improved process enable the reaction time to be stabilized. Based upon the new findings, the present invention has been completed.

Means to Solve the Problem

The present inventions are as follows.

Term 1:

A process for preparing a quaternary ammonium salt of formula (4):

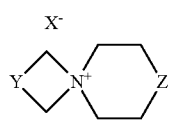
(4)

wherein

X is halogen atom, $C_{1-6}$ alkylsulfonyloxy group, or $C_{6-10}$ arylsulfonyloxy group, and $X^-$ is a counteranion thereof, Y is a substituent of the following formula (2a) or (2b):

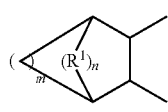
(2a)

(2b)

wherein $R^1$ is independently methylene or oxygen atom; $R^2$ is independently $C_{1-6}$ alkyl group, $C_{1-6}$ alkoxy group, or hydroxy group; m and n are independently 0, 1, 2, or 3; and p is 1 or 2, and Z is =N—$R^3$ or —CH—$R^4$ wherein $R^3$ is $C_{1-6}$ alkyl group, $C_{3-7}$ cycloalkyl group, $C_{5-7}$ cycloalkenyl group, $C_{6-10}$ aryl group, or 5- to 10-membered monocyclic or bicyclic heteroaryl group; $R^4$ is $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, or 5- to 10-membered monocyclic or bicyclic heteroarylthio group, comprising reacting a compound of formula (1):

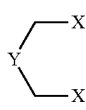
(1)

wherein X is independently selected from the above-defined ones, and Y is as defined above, with 1.5 to 15 mole of a compound of formula (3):

(3)

wherein Z is as defined above, per one mole of the compound of formula (1)

to prepare the quaternary ammonium salt of formula (4).

Term 2:

The process of Term 1 wherein the reaction of Compound (1) with Compound (3) includes the following steps (i) and (ii):

step (i): reacting Compound (1) with 0.1 to 1.0 mole of compound (3) per one mole of Compound (1), and then step (ii): adding the rest of Compound (3) to the reaction mixture so that the total amount of Compound (3) can be 1.5 to 15 mole per one mole of Compound (1), and continuing the reaction.

Term 3:

The process of Term 1 wherein the reaction of Compound (1) with Compound (3) includes the following steps (i) and (ii):

step (i): reacting 0.1 to 1.0 mole of Compound (1) with 0.1 to 1.0 mole of Compound (3) per one mole of the total amount of compound (1), and then step (ii): adding the rest of Compound (1) and the rest of Compound (3) to the reaction mixture so that the total amount of Compound (3) can be 1.5 to 15 mole per one mole of the total amount of Compound (1), and continuing the reaction.

Term 4:

The process of Term 2 or 3 wherein the reaction is carried out in the presence of 0.1 to 1.0 mole of an inorganic salt per one mole of the total amount of Compound (1).

Term 5:

The process of Term 4 wherein the inorganic salt is potassium carbonate.

Term 6:

The process of Term 4 or 5 wherein the amount of an inorganic salt is 0.1 to 0.3 mole per one mole of the total amount of Compound (1).

Term 7:

The process of any one of Terms 2 to 6 wherein the amount of Compound (3) added in step (i) is 0.1 to 0.5 mole per one mole of the total amount of Compound (1).

Term 8:

The process of any one of Terms 2 to 7 wherein the total amount of Compound (3) in step (ii) is 1.8 to 5 mole per one mole of Compound (1).

Term 9:

The process of any one of Terms 1 to 8 wherein X is independently $C_{1-6}$ alkylsulfonyloxy group, or $C_{6-10}$ arylsulfonyloxy group.

Term 10:

The process of Term 9 wherein X is methanesulfonyloxy group.

Term 11:

The process of any one of Terms 1 to 10 wherein Y is the substituent of formula (2a).

Term 12:

The process of Term 11 wherein m is 2 and n is 0.

Term 13:

The process of any one of Terms 1 to 12 wherein Z is =N—$R^3$.

Term 14:

The process of Term 13 wherein $R^3$ is 5- to 10-membered monocyclic or bicyclic heteroaryl group.

Term 15:

The process of term 14 wherein $R^3$ is 1,2-benzisothiazol-3-yl.

Term 16:
The process of any one of Terms 1 to 8 wherein the compound of formula (1) is

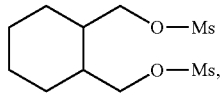

the compound of formula (3) is

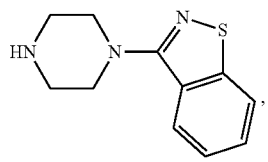 [SMILES: c1ccc2c(N3CCNCC3)nsc2c1]

and
the quaternary ammonium salt of formula (4) is

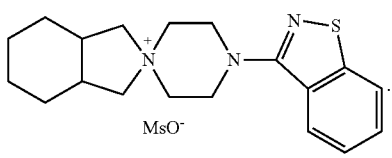

Term 17:
A process for preparing a compound of formula (8):

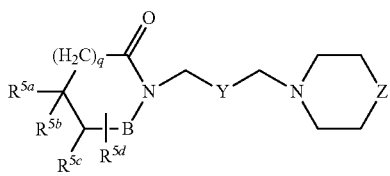
(8)

wherein
B is carbonyl group or sulfonyl group,
$R^{5a}$, $R^{5b}$, $R^{5c}$, and $R^{5d}$ are independenly hydrogen atom or $C_{1-4}$ alkyl group, alternatively $R^{5a}$ and $R^{5b}$, or $R^{5a}$ and $R^{5c}$ may be taken together to form a hydrocarbon ring, or $R^{5a}$ and $R^{5c}$ may be taken together to form an aromatic hydrocarbon ring, wherein the hydrocarbon ring may be bridged with $C_{1-4}$ alkylene or oxygen atom wherein the $C_{1-4}$ alkylene and the hydrocarbon ring may be substituted with at least one $C_{1-4}$ alkyl,
q is 0 or 1, and
Y and Z are as defined in term 1,
comprising reacting the quaternary ammonium salt (4) prepared according to any one of terms 1 to 16 with the following compound (7):

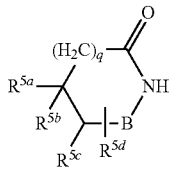
(7)

wherein B, $R^{5a}$, $R^{5b}$, $R^{5c}$, $R^{5d}$, and q are as defined above, in the presence of a solid inorganic base.
Term 18:
The process of Term 17 wherein B is carbonyl group.
Term 19:
The process of Term 17 or 18 wherein $R^{5a}$ and $R^{5c}$ are taken together to form a hydrocarbon ring which may be bridged with $C_{1-4}$ alkylene, and $R^{5b}$ and $R^{5d}$ are hydrogen atom.
Term 20:
The process of Term 19 wherein Compound (7) is the following compound of formula (7b):

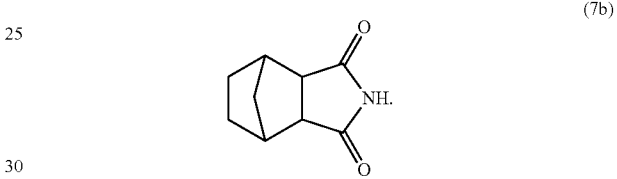
(7b)

Term 21:
The process of any one of Terms 17 to 20 wherein Compound (8) is (3aR,4S,7R,7aS)-2-{(1R,2R)-2-[4-(1,2-benzisothiazol-3-yl)piperazin-1-ylmethyl]cyclohexylmethyl}-hexahydro-4,7-methano-2H-isoindole-1,3-dione.

Effect of the Invention

According to the present invention, in the process for preparing the quaternary ammonium salt of the above formula (4) (hereinafter, abbreviated as "quaternary ammonium salt (4)"), the reaction can be done with a steady repeatability of the reaction time while the production of by-product (R) can be held down. Furthermore, according to the present invention, the process for preparing the compound of formula (8) or an acid addition salt thereof which is known as a medicament for treating schizophrenia or similar diseases, for example, (3aR,4S,7R,7aS)-2-{(1R,2R)-2-[4-(1,2-benzisothiazol-3-yl)-piperazin-1-yl-methyl]cyclohexylmethyl}hexahydro-4,7-methano-2H-isoindole-1,3-dione (2-[[(1R,2R)-2-[[4-(1,2-benzisothiazol-3-yl)-1-piperazinyl]methyl]cyclohexyl]methyl]hexahydro-(3aS,4R,7S,7aR)-4,7-methano-1H-isoindole-1,3(2H)-dione), can be done in high purity and high efficiency.

It is thought that the present invention can make the production of by-product (R) held down and make the reaction time stabilized in the mechanism mentioned below. Namely, the compound of formula (3) (hereinafter, abbreviated as "Compound (3)") can be reacted with the compound of formula (1) (hereinafter, abbreviated as "Compound (1)") to prepare quaternary ammonium salt (4) while Compound (3) works as a base with its internal amino group, and simultaneously the rest of Compound (3) forms a salt with "X" originated from Compound (1) to prepare the compound of formula (5):

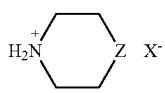

(5)

wherein X⁻ is the above-mentioned counteranion, and Z is as defined above (hereinafter, abbreviated as "Compound (5)") which does not engage in the reaction. Accordingly, Compound (3) in the reaction becomes insufficient and then the reaction time comes to be unstabilized. In the present invention, an excess amount of Compound (3) is used, thus Compound (3) does not run short and the reaction can be steadily carried out (i.e. shortening the reaction time and enhancing the transformation rate) even though Compound (5) is produced. In addition, potassium carbonate which is used as a base for reviving Compound (3) from Compound (5) can be deleted or reduced in the present invention, thus the present invention can hold down the producing of by-product (R) and make it possible to prepare quaternary ammonium salt (4) in stably high quality, particularly with an industrial advantage. Particularly, in an industrial scale process, it is possible to shorten the reaction time and enhance the transformation rate.

BEST MODE FOR CARRYING OUT THE INVENTION

Hereinafter, the present invention is further illustrated. The number additionally-described in each "substituent" such as "$C_{1-6}$" means the number of carbons contained therein. For example, "$C_{1-6}$ alkyl" means an alkyl group having 1 to 6 carbon atoms.

The number of substituents defined in an "optionally substituted" or "substituted" group is not limited as long as the substitution is possible, and the number may be one or more. Each substituent used herein may be applied as a part of other substituent or a substituent of other substituent, unless otherwise indicated.

The term "halogen atom" used herein includes, for example, fluorine atom, chlorine atom, bromine atom and iodine atom, and preferably fluorine atom or chlorine atom.

The term "$C_{1-6}$ alkyl group" used herein means a straight or branched chain saturated hydrocarbon group having 1-6 carbon atoms, and the preferable one is "$C_{1-4}$ alkyl group". The "$C_{1-6}$ alkyl group" includes, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{3-7}$ cycloalkyl group" used herein means a cyclic saturated hydrocarbon group having 3-7 carbon atoms, and the preferable one is "$C_{3-6}$ cycloalkyl group". The "$C_{3-7}$ cycloalkyl group" includes, for example, cyclopropyl, cyclobutyl, cyclopentyl, and cyclohexyl.

The term "$C_{6-10}$ aryl group" used herein means an aromatic hydrocarbon group having 6-10 carbon atoms, and the preferable one is "$C_6$ aryl group" (i.e. phenyl). The "$C_{6-10}$ aryl group" includes, for example, phenyl, 1-naphthyl and 2-naphthyl.

The term "$C_{1-6}$ alkoxy group" used herein means a $C_{1-6}$ alkyloxy group, wherein the $C_{1-6}$ alkyl moiety is defined as the above-mentioned "$C_{1-6}$ alkyl", and the preferable one is "$C_{1-4}$ alkoxy group". The "$C_{1-6}$ alkoxy group" includes, for example, methoxy, ethoxy, propoxy, isopropoxy, butoxy, isobutoxy, sec-butoxy, and tert-butoxy.

The term "$C_{3-7}$ cycloalkoxy group" used herein means a $C_{3-7}$ cycloalkyloxy group, wherein the $C_{3-7}$ cycloalkyl moiety is defined as the above-mentioned "$C_{3-7}$ cycloalkyl". The "$C_{3-7}$ cycloalkoxy group" includes, for example, cyclopropyloxy, cyclobutyloxy, cyclopentyloxy, and cyclohexyloxy.

The "$C_{6-10}$ aryl" moiety in the term "$C_{6-10}$ aryloxy group" used herein is defined as the above-mentioned "$C_{6-10}$ aryl", and the preferable "$C_{6-10}$ aryloxy group" is "$C_6$ aryloxy" (i.e. phenyloxy). The "$C_{6-10}$ aryloxy group" includes, for example, phenoxy, 1-naphthyloxy and 2-naphthyloxy.

The "$C_{1-6}$ alkyl" moiety in the term "$C_{1-6}$ alkylthio group" used herein is defined as the above-mentioned "$C_{1-6}$ alkyl", and the preferable "$C_{1-6}$ alkylthio group" is "$C_{1-4}$ alkylthio group". The "$C_{1-6}$ alkylthio group" includes, for example, methylthio, and ethylthio.

The "$C_{3-7}$ cycloalkyl" moiety in the term "$C_{3-7}$ cycloalkylthio group" used herein is defined as the above-mentioned "$C_{3-6}$ cycloalkyl". The "$C_{3-7}$ cycloalkylthio group" includes, for example, cyclopropylthio, cyclobutylthio, cyclopentylthio, and cyclohexylthio.

The "$C_{6-10}$ aryl" moiety in the term "$C_{6-10}$ arylthio group" used herein is defined as the above-mentioned "$C_{6-10}$ aryl". The "$C_{6-10}$ arylthio group" includes, for example, phenylthio, 1-naphthylthio and 2-naphthylthio.

The "$C_{1-6}$ alkyl" moiety in the term "$C_{1-6}$ alkylsulfonyloxy group" used herein is defined as the above-mentioned "$C_{1-6}$ alkyl", and the preferable "$C_{1-6}$ alkylsulfonyloxy group" is "$C_{1-4}$ alkylsulfonyloxy group".

The "$C_{1-6}$ alkylsulfonyloxy group" includes, for example, methylsulfonyloxy, and ethylsulfonyloxy.

The "$C_{6-10}$ aryl" moiety in the term "$C_{6-10}$ arylsulfonyloxy group" used herein is defined as the above-mentioned "$C_{6-10}$ aryl". The "$C_{6-10}$ arylsulfonyloxy group" includes, for example, phenylsulfonyloxy, 1-naphthylsulfonyloxy and 2-naphthylsulfonyloxy.

The "heteroaryl group" used herein includes, for example, a 5- to 10-membered monocyclic or multi-cyclic aromatic group having one or more heteroatoms (e.g. 1 to 4 heteroatoms) independently-selected from nitrogen, sulfur, and oxygen atom. The "multi-cyclic heteroaryl group" preferably includes a bicyclic or tricyclic one, and more preferably a bicyclic one. The "multi-cyclic heteroaryl group" also includes a fused cyclic group of the above-mentioned monocyclic heteroaryl group with the above-mentioned aromatic ring group (e.g. benzene) or non-aromatic ring group (e.g. cyclohexyl). The "heteroaryl group" includes, for example, the following groups.

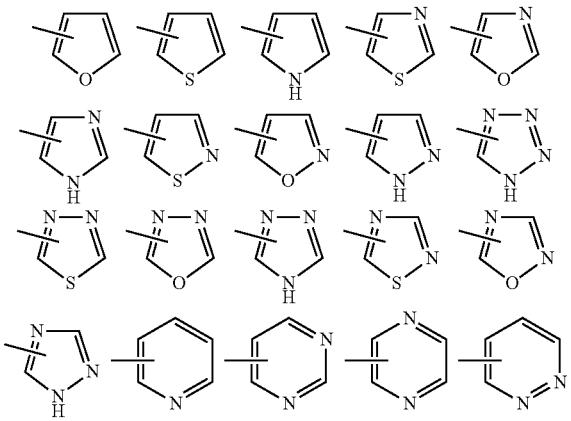

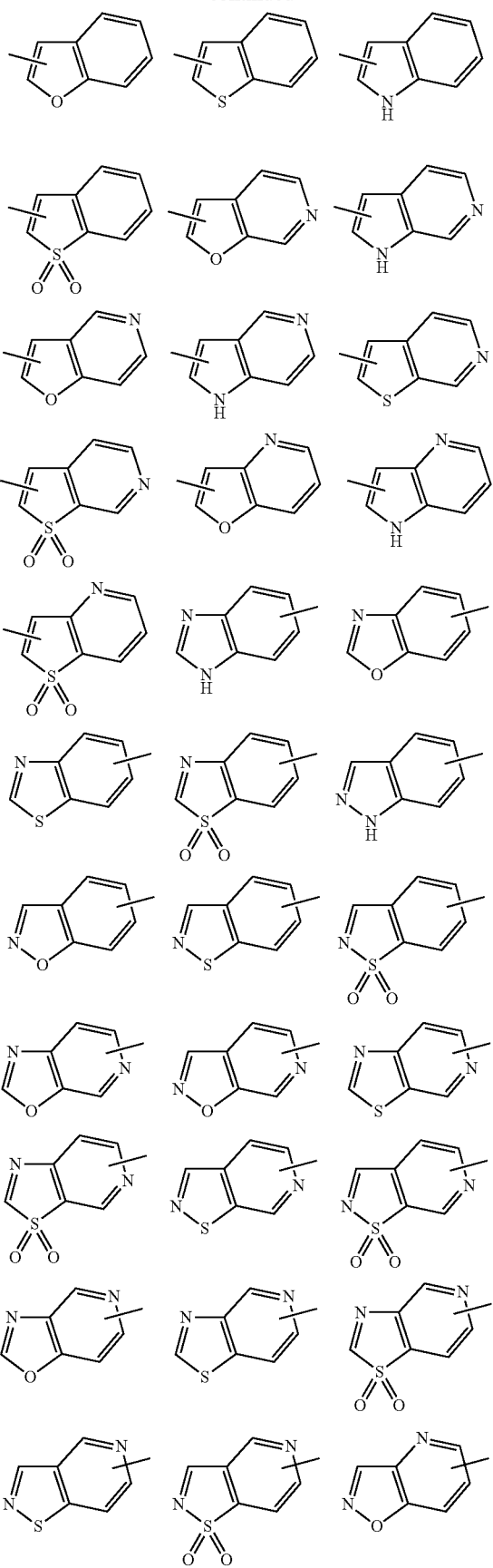

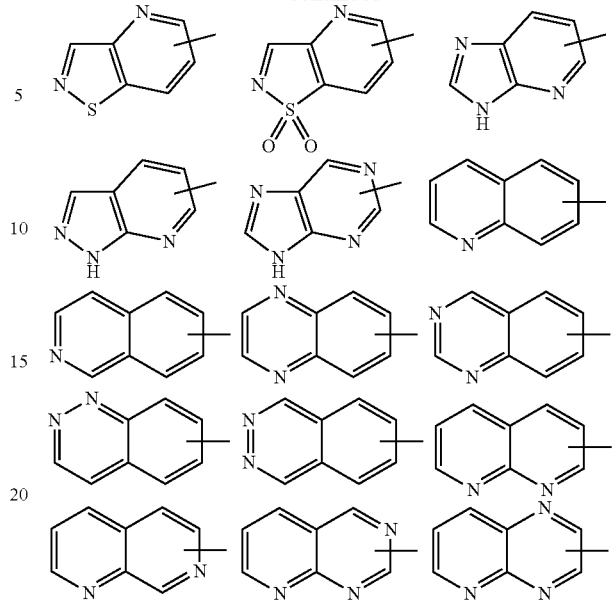

The bond used herein which is connected to the middle of a bond in a ring compound is meant to be attached to any possible position of the ring. For example, the heteroaryl group of the following formula:

means 2-furyl group, or 3-furyl group.

In case that "heteroaryl group" is a multiple-cyclic group, for example, in case of the following group:

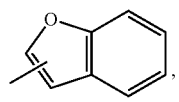

it means 2-benzofuryl group, or 3-benzofuryl group, and additionally, it may mean 4-, 5-, 6- or 7-benzofuryl group. However, in case that a multiple-cyclic heteroaryl group which is composed by fusing an aromatic ring and non-aromatic ring (e.g. piperidine), only the positions in the aromatic ring have the bond. For example, the "multiple-cyclic heteroaryl group" such as the following group:

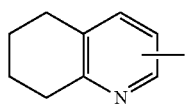

means to be bound on 2-, 3-, or 4-position.

The "heteroaryl" moiety in the term "heteroaryloxy group" used herein is defined as the above-mentioned "heteroaryl group". The "heteroaryloxy group" includes, for example, pyridyloxy.

The "heteroaryl" moiety in the term "heteroarylthio group" used herein is defined as the above-mentioned "heteroaryl group". The "heteroarylthio group" includes, for example, pyridylthio.

The "$C_{5-7}$ cycloalkenyl group" used herein includes a cycloalkenyl group having 5-7 carbon atoms such as cyclopentenyl group, cyclohexenyl group, and cycloheptenyl group.

The "$C_{5-7}$ cycloalkenyloxy group" used herein includes a group composed of the above-mentioned cycloalkenyl group and oxygen atom, such as cyclopentenyloxy group.

The "$C_{5-7}$ cycloalkenylthio group" used herein includes the above-mentioned cycloalkenyloxy group wherein the oxygen atom is replaced by sulfur atom, such as cyclohexylthio group.

The "$C_{1-4}$ alkylene" used herein has 1-4 carbon atoms and includes, for example, methylene, ethylene, and trimethylene.

The "$C_{1-3}$ alkylene" used herein has 1-3 carbon atoms and includes, for example, methylene, ethylene, and trimethylene.

The "hydrocarbon ring" used herein is a cyclic alkane having 3-7 carbon atoms such as $C_{3-7}$ cycloalkane, or a cyclic alkene having 5-7 carbon atoms such as $C_{5-7}$ cycloalkene. The cyclic alkane having 3-7 carbon atoms includes, for example, cyclopropane, cyclobutane, cyclopentane, cyclohexane, cycloheptane. The cyclic alkene having 5-7 carbon atoms includes, for example, cyclopentene, cyclohexene, and cycloheptene.

The "aromatic hydrocarbon ring" used herein means a ring containing the above-mentioned "$C_{6-10}$ aryl" moiety.

The "counteranion" includes, for example, halogen ion (e.g. chlorine ion), sulfate ion, hydrogensulfate ion, phosphate ion, hydrogenphosphate ion, dihydrogenphosphate ion, $C_{1-6}$ alkylsulfonate ion (e.g. methanesulfonate ion), $C_{6-10}$ arylsulfonate ion (e.g. p-toluenesulfonate ion), and hydroxide ion.

The "by-product which is produced by the reaction with potassium carbonate wherein the by-product has a carbonate part therein" (by-product (R)) is all-inclusive term of by-products having at least one carbonate parts therein. In the present specification, these by-products are expressed as "by-product (R)", and the producing rates of by-product (R) in the examples mentioned below are used as an evaluation of the present invention.

Compound (1) includes, for example, 1,4-dibromobutane, 1,4-dichlorobutane, 1,4-diiodobutane, 1,4-dimethanesulfonyloxybutane, 1,4-di(p-toluenesulfonyloxy)-butane, 2-hydroxy-1,3-dibromopropane, 2-hydroxy-1,3-dichloropropane, 2-hydroxy-1,3-dimethanesulfonyloxypropane, 1,2-bis(bromomethyl)cyclohexane, 1,2-bis(methanesulfonyloxymethyl)cyclohexane, 1,2-bis(bromomethyl)cyclopentane, 1,2-bis(methanesulfonyloxymethyl)cyclopentane, 2,3-bis(bromomethyl)-bicyclo[2.2.1]heptane, 2,3-bis(methane-sulfonyloxymethyl)-bicyclo[2.2.1]heptane, 4,5-bis(bromo-methyl)-1-cyclohexene, 4,5-bis(methane-sulfonyloxymethyl)-1-cyclohexene, and 2,3-bis(bromomethyl)-7-oxabicyclo[2.2.1]-hept-5-ene.

As Compound (1) used herein, a commercially available compound may be used. In case that Compound (1) has a chiral carbon(s), i.e. it has an optical isomer, the compound herein may be a single optical isomer, a racemic compound thereof, or a mixture of optical isomers in a certain ratio.

A preferable example of Compound (1) includes a compound of the following formula:

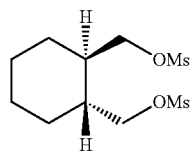

wherein Ms means methanesulfonyl group.

In Compound (3), $C_{1-6}$ alkyl group, $C_{3-7}$ cycloalkyl group, $C_{5-7}$ cycloalkenyl group, $C_{6-10}$ aryl group, and 5- to 10-membered monocyclic or bicyclic heteroaryl group in "$R^3$"; and $C_{1-6}$ alkyl group, $C_{1-6}$ alkoxy group, $C_{1-6}$ alkylthio group, $C_{3-7}$ cycloalkyl group, cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, and 5- to 10-membered monocyclic or bicyclic heteroarylthio group in "$R^4$" may be further optionally substituted with the same or different one to three substituents selected from the group consisting of $C_{1-4}$ alkyl, $C_{1-4}$ alkoxy, $C_{1-4}$ alkylthio and halogen atom.

Compound (3) includes, for example, 4-phenylpiperazine, 4-(2methoxyphenyl)piperazine, 4-cyclohexylpiperazine, 4-(2-pyridinyl)piperazine, 4-(2-pyrimidinyl)piperazine, 4-(2-quinolyl)piperazine, 4-(4-quinolyl)piperazine, 4-(1,2-benzisothiazol-3-yl)piperazine, 4-(4-fluorophenyl)piperidine, 4-[(4-fluorophenyl)thio]-piperidine, 4-(3-chlorophenyl)piperazine, 4-(1,2-benzisoxazol-3-yl)piperidine, 4-(5-benzofuranyl)piperazine, 4-(1-naphthyl)piperazine, 4-[bis(4-fluorophenyl)methylene]-piperidine, 4-(3-isoquinolyl)piperazine, 4-(8-quinolyl)-piperazine, 4-(7-benzofuranyl)piperazine, and 4-(5-fluoro-1,2-benzisoxazol-3-yl)piperidine. The preferable example is 4-(1,2-benzisothiazol-3-yl)piperazine.

Compound (3) can be prepared according to, for example, JP 63 (1988)-83085 A, J. Med. Chem., 28761 (1985), and J. Med. Chem., 32, 1024 (1989). And, Compound (3) may include an addition acid salt thereof (3) such as a hydrochloride and a sulfate thereof.

In the reaction between Compound (1) and Compound (3) in the present invention, Compound (3) is used in an excess amount for Compound (1). The amount of Compound (3) used herein is preferably 1.5 mole to 15 mole per one mole of Compound (1), more preferably, 1.8 mole to 5 mole per one mole of Compound (1), typically 2 mole per one mole of Compound (1). The upper limit amount of Compound (3) used herein is not limited, but, in case that the amount is too much, the by-product of formula (6):

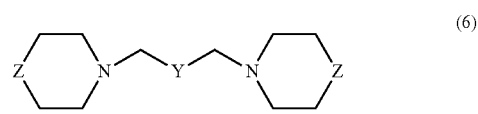

(6)

wherein Y and Z are as defined in the above Term 1 (hereinafter, abbreviated as "by-product (6)") tends to increase. Accordingly, the amount of Compound (3) used is practically not more that 5 mole per one mole of Compound (1). The reaction can proceed without potassium carbonate when 2 mole of Compound (3) is used per one mole of Compound (1), hence quaternary ammonium salt (4) of formula (4):

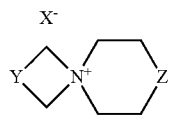
(4)

wherein X, Y and Z are as defined in the above Term 1, can be prepared with a steady quality while the production of by-product (R) can be held down.

In the present invention, it is possible to react Compound (1) and Compound (3) in two steps (in two-step addition). Namely, it is preferable to react each partial amount of Compound (1) and Compound (3) firstly, and then add the rests of Compound (1) and Compound (3) to the reaction mixture to complete the reaction. In detail, it is more preferable to react 0.1 to 1.0 time of Compound (1) per the total amount of Compound (1) and 0.1 to 1.0 time of Compound (3) per the total amount of Compound (1) (step i), then add the rest of Compound (1) and 1.8 to 5.0 times of Compound (3) per the total amount of Compound (1) to the reaction mixture to complete the reaction (step ii).

In the reaction between Compound (1) and Compound (3), a solid inorganic base (salt) may be coexistent. The solid inorganic base (salt) includes, for example, an alkali metal carbonate such as potassium carbonate, and sodium carbonate; an alkali earth metal salt such as calcium carbonate, and magnesium carbonate; and an alkali metal bicarbonate such as sodium bicarbonate, and potassium bicarbonate; preferably an alkali metal carbonate, in particular, potassium carbonate. Such solid inorganic base may be used alone or as a mixture of two or more kinds of bases. And, such solid inorganic base may be an anhydrous form or a hydrate thereof.

The upper limit amount of the solid inorganic base used herein is not limited, but, in case that the amount is too much, by-products increases. Accordingly, the general amount of the solid inorganic base used is preferably 0.1 to 0.3 mole per one mole of the total amount of Compound (1). And, in case of using an acid addition salt of Compound (3), it is preferable to add an additional appropriate amount of a base to neutralize the acid addition salt.

If Compound (5) of formula (5):

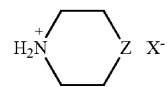
(5)

wherein X⁻ is an counteranion, and Z is as defined in the above Term 1, precipitates as an oil, not as a crystal in the reaction, i.e. the aspect of the reaction solution is not good, the aspect can be improved by add a crystal seed of Compound (5) thereto to promote the crystallization of Compound (5). Or, it is also possible to improve it by preparing a small amount of the crystal seed of Compound (5) in the pre-reaction, and then reacting Compound (1) and Compound (3). However, Compound (5) cannot sometimes be crystallized due to its property.

The solvent used herein includes, for example, an alcohol solvent such as methanol, and ethanol; an aprotic polar solvent such as acetonitrile, and N,N-dimethylformamide; aromatic carbon ring solvent such as toluene, and xylene; which can be used alone or in a mixture of two or more kinds of the solvents and the amount of the solvent used is not limited.

The reaction temperature is generally 60 to 180° C., preferably 90 to 150° C.

After the reaction is completed, for example, the reaction mixture or a part of the reaction mixture can be concentrated and then filtrated to give a mixture of the quaternary ammonium salt (4) and Compound (5). In addition, the reaction mixture containing quaternary ammonium salt (4) and Compound (5) may be used in the reaction mentioned below without taking out quaternary ammonium salt (4) from the mixture.

Quaternary ammonium salt (4) thus prepared includes, for example, chloride, bromide, iodide, hydroxide, sulfate, hydrogensulfate, phosphate, hydrogenphosphate, dihydrogen-phosphate, methanesulfonate, and p-toluenesulfonate of 7-cyclohexyl-2-hydroxy-7-aza-4-azoniaspiro[3.5]-nonane,
8-phenyl-8-aza-5-azoniaspiro[4.5]decane,
8-(2-methoxyphenyl)-8-aza-5-azoniaspiro[4.5]decane,
8-(2-pyridinyl)-8-aza-5-azoniaspiro[4.5]decane,
8-(2-pyrimidinyl)-8-aza-5-azoniaspiro[4.5]decane,
8-(2-quinolyl)-8-aza-5-azoniaspiro[4.5]decane,
8-(4-quinolyl)-8-aza-5-azoniaspiro[4.5]decane,
8-(1,2-benzisothiazol-3-yl)-8-aza-5-azoniaspiro-[4.5]decane,
4'-(1,2-benzisothiazol-3-yl)octahydro-spiro[2H-isoindole-2,1'-piperazinium],
4'-[(4-fluorophenyl)thio]octahydro-spiro[2H-isoindole-2,1'-piperidinium],
4'-(2-pyrimidinyl)octahydro-spiro[2H-isoindole-2,1'-piperazinium],
4'-(4-fluorophenoxy)octahydro-spiro[2H-isoindole-2,1'-piperidinium],
4'-(1,2-benzisoxazol-3-yl)octahydro-spiro[2H-isoindole-2,1'-piperidinium],
4'-(6-fluoro-1,2-benzisoxazol-3-yl)-octahydro-spiro[2H-isoindole-2,1'-piperazinium],
4'-(2-pyridinyl)octahydro-spiro[2H-isoindole-2,1'-piperazinium],
4'-(3-chlorophenyl)octahydro-spiro[2H-isoindole-2,1'-piperazinium],
4'-(5-benzofuranyl)octahydro-spiro[2H-isoindole-2,1'-piperazinium],
4'-(1-naphthyl)octahydro-spiro[2H-isoindole-2,1'-piperazinium],
4'-[bis(4-fluorophenyl)methylene]octahydro-spiro[2H-isoindole-2,1'-piperidinium],
4'-(2-methoxyphenyl)octahydro-spiro[2H-isoindole-2,1'-piperazinium],
4'-(3-isoquinolyl)octahydro-spiro[2H-isoindole-2,1'-piperazinium],
4'-(8-quinolyl)octahydro-spiro[2H-isoindole-2,1'-piperazinium],
4'-(1,2-benzisothiazol-3-yl)tetrahydro-spiro-[cyclopenta[c]pyrrole-2(1H), 1'-piperazinium],
4'-(1,2-benzisothiazol-3-yl)octahydro-spiro[4,7-methano-2H-isoindole-2,1'-piperazinium],
4'-(1,2-benzisothiazol-3-yl)-1,3,3a,4,7,7a-hexahydro-spiro[2H-isoindole-2,1'-piperazinium],
4'-(1,2-benzisothiazol-3-yl)-1,3,3a,4,7,7a-hexahydro-spiro[4,7-epoxy-2H-isoindole-2,1'-piperazinium], or
4'-(7-benzofuranyl)octahydro-spiro[2H-isoindole-2,1'-piperazinium].

By reacting the resulting quaternary ammonium salt (4) and a compound of formula (7):

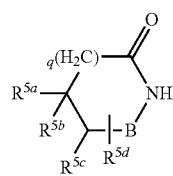

(7)

wherein the symbols are as defined in the above Term 17 (hereinafter, abbreviated as "Compound (7)") in the presence of a solid inorganic base, an imide compound of formula (8):

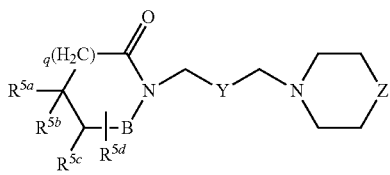

(8)

wherein the symbols are as defined in the above Term 17 (hereinafter, abbreviated as "imide compound (8)") can be prepared.

Compound (7) includes a compound of the following formula (7a):

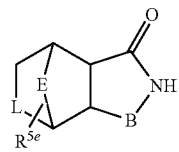

(7a)

wherein -L- is a single or double bond, E is $C_{1-3}$ alkylene optionally substituted with $C_{1-4}$ alkyl or oxygen atom, $R^{5e}$ is hydrogen atom or $C_{1-4}$ alkyl group, and B is as defined in the above formula (7).

Compound (7) includes, for example, succinimide, 2,6-piperidine-dione, 4,4-dimethyl-2,6-piperidine-dione, 8-azaspiro[4.5]decane-7,9-dione, perhydroazepin-2,7-dione, maleimide, phthalimide, tetrahydrophthalimide, cis-1,2-cyclohexane-dicarboximide, trans-1,2-cyclohexane-dicarboximide, cis-1,2-cyclohex-4-ene-dicarboximide, trans-1,2-cyclohex-4-ene-dicarboximide, cis-4-methyl-1,2-cyclohexane-dicarboximide, trans-4-methyl-1,2-cyclohexane-dicarboximide, cis-1,2-dimethyl-1,2-cyclohexane-dicarboximide, trans-1,2-dimethyl-1,2-cyclohexane-dicarboximide, cis-4,5-dimethyl-1,2-cyclohexane-dicarboximide, trans-4,5-dimethyl-1,2-cyclohexane-dicarboximide, cis-3,6-dimethyl-1,2-cyclohexane-dicarboximide, trans-3,6-dimethyl-1,2-cyclohexane-dicarboximide, bicyclo[2.2.1]heptane-2,3-di-exo-carboximide, bicyclo[2.2.1]heptane-2,3-di-endo-carboximide, bicyclo[2.2.1]hept-5-ene-2,3-di-exo-carboximide, bicyclo-[2.2.1]hept-5-ene-2,3-di-endo-carboximide, bicyclo[2.2.2]-octane-2,3-di-exo-carboximide, bicyclo[2.2.2]octane-2,3-di-endo-carboximide, bicyclo[2.2.2]oct-5-ene-2,3-di-exo-carboximide, bicyclo[2.2.2]oct-5-ene-2,3-di-endo-carboximide, bicyclo[2.2.2]oct-7-ene-2,3-di-exo-carboximide, bicyclo[2.2.2]oct-7-ene-2,3-di-endo-carboximide, hexahydro-4,7-methano-1,2-benzisothiazol-3(2H)-one-1,1-dioxide, 3,6-epoxy-1,2-cyclohexane-dicarboximide, and spiro[bicyclo[2.2.2]octane-2,3'-pyrrolidine]-2',5'-dione.

A preferable example of Compound (7) includes a compound of the following (7b):

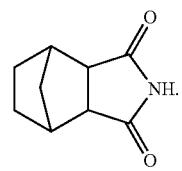

(7b)

Compound (7b) can include its optical isomers, thus the compound used herein may be one of the optical isomers or a mixture of the optical isomers. A preferable example of Compound (7) includes a compound of the following formula:

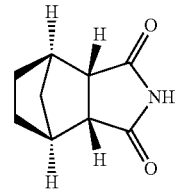 [SMILES: O=C1NC(=O)[C@H]2[C@@H]3CC[C@@H](C3)[C@@H]12]

or a salt thereof.

Compound (7) can be prepared, for example, by reacting a corresponding carboxylic anhydride compound and ammonia (for example, JP-1(1989)-199967 A).

The solid inorganic base (salt) includes, for example, an alkali metal carbonate such as potassium carbonate, and sodium carbonate; an alkali earth metal salt such as calcium carbonate, and magnesium carbonate; and an alkali metal bicarbonate such as sodium bicarbonate, and potassium bicarbonate; preferably an alkali metal carbonate, in particular, potassium carbonate. Such solid inorganic base may be used alone or as a mixture of two or more kinds of bases. And, such solid inorganic bases may be an anhydrous form or a hydrate thereof.

The amount of the solid inorganic base used herein is generally 0.7 mole or more, preferably 0.9 mole or more per one mole of the total amount of Compound (1) or quaternary ammonium salt (4). The upper limit amount of the solid inorganic base used herein is not limited, but, in case that the amount is too much, the process cost increases. Accordingly, the practical amount of the solid inorganic base is 3 mole or less, preferably 2.7 mole or less per one mole of the total amount of Compound (1) or quaternary ammonium salt (4).

The amount of Compound (7) used herein is generally 0.7 mole or more per one mole of the total amount of Compound (1) or quaternary ammonium salt (4). The upper limit amount of Compound (7) used herein is not limited, but, in case that the amount is too much, the process cost increases. Accordingly, the practical amount of Compound (7) is 2.5 mole or less per one mole of the total amount of Compound (1) or quaternary ammonium salt (4).

The reaction of the present invention is generally carried out in the presence of a solvent. The solvent used herein includes, for example, aromatic hydrocarbons such as toluene, xylene, mesitylene, chlorobenzene, and dichlorobenzene. The amount of such solvent used herein is generally 3 parts by weight or more, preferably 5 parts by weight or more per one part by weight of the total amount of Compound (1) or quaternary ammonium salt (4). The upper limit amount of the solvent used herein is not limited, but, in case that the amount is too much, the volumetric efficiency is turned down. Accordingly, the practical amount of the solvent is 20 parts by weight or less per one part by weight of the total amount of Compound (1) or quaternary ammonium salt (4).

The reaction of the present invention is preferably carried out in the coexistence of water, i.e. in the presence of generally 0.05 to 3 mole, preferably 0.1 to 1.5 mole of water per one mole of the total amount of Compound (1) or quaternary ammonium salt (4). When using a hydrate of solid inorganic base, the amount of water used herein may be decided considering the water of the hydrate. The water may initially exist in the reaction medium or an appropriate amount of water may be added thereto in mid-course. Or, the water may be added to Compound (7) and/or quaternary ammonium salt (4) beforehand.

In addition, the reaction of the present invention may be carried out in the coexistence of a phase-transfer catalyst such as tetra-n-butyl ammonium hydrogen sulfate, tetra-n-butyl ammonium bromide, and benzyl triethyl ammonium chloride. The amount of the phase-transfer catalyst used herein is generally 0.01 to 0.5 mole per one mole of the total amount of Compound (1) or quaternary ammonium salt (4).

The reaction temperature is generally 80 to 180° C., preferably 95 to 150° C.

The reaction of quaternary ammonium salt (4) and Compound (7) is generally carried out by contacting and mixing quaternary ammonium salt (4), Compound (7) and a solid inorganic base, and the addition order of the substances is not limited. The solid inorganic base may be added thereto in separated amounts or in a lump, but it is preferable in a lump.

The reaction mixture containing imide compound (8) is obtained after the reaction, and the mixture can be treated by adding water thereto, mixing it, standing still in a whole, separating it with a separating funnel, optionally treating the organic layer with active carbon, and concentrating the organic layer to give imide compound (8). Alternatively, imide compound (8) can be obtained as a crystal by cooling the above-mentioned organic layer or the partially-concentrated organic layer, or adding another solvent which is comparatively insoluble for imide compound (8) to the organic layer. The solvent which is comparatively insoluble for imide compound (8) includes, for example, an aliphatic hydrocarbon solvent such as pentane, hexane, and heptane, and an alcohol solvent such as methanol, ethanol, and isopropanol.

In addition, imide compound (8) can be also obtained from the reaction mixture containing imide compound (8) by removing out insoluble precipitates with a filter and concentrating the filtrate. Further, imide compound (8) can be obtained as a crystal by cooling the reaction mixture or the partially-concentrated reaction mixture, or adding another solvent which is comparatively insoluble for imide compound (8) to the organic layer.

The obtained imide compound (8) may be further purified by a conventional purification such as recrystallization and chromatography. In addition, imide compound (8) can be obtained as an inorganic acid addition salt such as hydrochloride, sulfate, hydrobromide, and phosphate; or an organic acid addition salt such as acetate, oxalate, citrate, malate, tartrate, maleate, and fumarate.

The imide compound (8) prepared herein includes, for example,

2-[4-(4-phenyl-1-piperazinyl)butyl]hexahydro-1H-isoindole-1,3(2H)-dione,

2-[4-(4-phenyl-1-piperazinyl)butyl]hexahydro-4,7-methano-1H-isoindole-1,3(2H)-dione, 2-[4-[4-(2-methoxyphenyl)-1-piperazinyl]butyl]-hexahydro-1H-isoindole-1,3(2H)-dione, 2-[4-[4-(2-methoxyphenyl)-1-piperazinyl]butyl]-hexahydro-4,7-methano-1H-isoindole-1,3(2H)-dione, 2-[[2-[([4-(1,2-benzisothiazol-3-yl)-1-piperazinyl]-methyl]cyclohexyl]methyl]hexahydro-4,7-methano-1H-isoindole-1,3(2H)-dione (2-[2-[(4-(1,2-benzisothiazol-3-yl)piperazin-1-ylmethyl]cyclohexylmethyl]hexahydro-4,7-methano-2H-isoindole-1,3-dione), 2-[[2-[[4-(1,2-benzisothiazol-3-yl)-1-piperazinyl]-methyl]cyclohexyl]methyl]hexahydro-4,7-methano-1,2-benzisothiazole-3(2H)-one-1,1-dioxide, 2-[[2-[[4-(1,2-benzisothiazol-3-yl)-1-piperazinyl]-methyl]cyclohexyl]methyl]hexahydro-1H-isoindole-1,3(2H)-dione, 2-[[2-[[4-(2-pyrimidinyl)-1-piperazinyl]methyl]-cyclohexyl]methyl]hexahydro-4,7-methano-1H-isoindole-1,3(2H)-dione, 2-[[2-[[4-(1,2-benzisothiazol-3-yl)-1-piperazinyl]-methyl]cyclohexyl]methyl]-3a,4,7,7a-tetrahydro-1H-isoindole-1,3(2H)-dione, 8-[[2-[[4-(1,2-benzisothiazol-3-yl)-1-piperazinyl]-methyl]cyclohexyl]methyl]-8-azaspiro[4,5]decane-7,9-dione, 1-[[2-[[4-(1,2-benzisothiazol-3-yl)-1-piperazinyl]-methyl]cyclohexyl]methyl]-4,4-dimethyl-2,6-piperidine-dione, 2-[[2-[[4-(1,2-benzisothiazol-3-yl)-1-piperazinyl]-methyl]cyclohexyl]methyl]hexahydro-4,7-epoxy-1H-isoindole-1,3(2H)-dione, 1'-[[2-[[4-(1,2-benzisothiazol-3-yl)-1-piperazinyl]-methyl]cyclohexyl]methyl]-spiro[bicyclo[2.2.2]octane-2,3'-pyrrolidine]-2',5'-dione, 2-[[2-[[4-(1,2-benzisothiazol-3-yl)-1-piperazinyl]-methyl]cyclohexyl]methyl]hexahydro-3a,7a-dimethyl-1H-isoindole-1,3(2H)-dione, 2-[[2-[[4-(1,2-benzisothiazol-3-yl)-1-piperazinyl]-methyl]cyclohexyl]methyl]-3a,4,7,7a-tetrahydro-4,7-ethano-1H-isoindole-1,3(2H)-dione, 2-[[2-[[4-(1,2-benzisothiazol-3-yl)-1-piperazinyl]-methyl]cyclohexyl]methyl]hexahydro-4,7-ethano-1H-isoindole-1,3(2H)-dione, 2-[[2-[[4-(1,2-benzisothiazol-3-yl)-1-piperazinyl]-methyl]cyclohexyl]methyl]-1H-isoindole-1,3(2H)-dione, 2-[[2-[[4-(1,2-benzisothiazol-3-yl)-1-piperazinyl]-methyl]cyclohexyl]methyl]-4,5,6,7-tetrahydro-1H-isoindole-1,3(2H)-dione, 2-[[2-[[4-[(4-fluorophenyl)thio]-1-piperidyl]-methyl]cyclohexyl]methyl]hexahydro-4,7-methano-1H-isoindole-1,3(2H)-dione, 2-[[2-[[4-[(4-fluorophenyl)thio]-1-piperidyl]methyl]cyclohexyl]methyl]hexahydro-1H-isoindole-1,3(2H)-dione, 2-[[2-[[4-(4-fluorophenoxy)-1-piperidyl]methyl]-cyclohexyl]methyl]hexahydro-4,7-methano-1H-isoindole-1,3(2H)-dione, 2-[[2-[[4-(4-fluorophenoxy)-1-piperidyl]methyl]-cyclohexyl]methyl]hexahydro-1H-isoindole-1,3(2H)-dione, 2-[[2-[[4-(1,2-benzisoxazol-3-yl)-1-piperidyl]-methyl]cyclohexyl]methyl]hexahydro-4,7-methano-1H-isoindole-1,3(2H)-dione, 2-[[2-[[4-(1,2-benzisoxazol-3-yl)-1-piperidyl]-methyl]cyclohexyl]methyl]hexahydro-1H-isoindole-1,3(2H)-dione, 2-[[2-[[4-(6-fluoro-1,2-benzisoxazol-3-yl)-1-piperidyl]methyl]cyclohexyl]methyl]hexahydro-4,7-methano-1H-isoindole-1,3(2H)-dione, 2-[[2-[[4-(6-fluoro-1,2-benzisoxazol-3-yl)-1-piperidyl]methyl]cyclohexyl]methyl]hexahydro-1H-isoindole-1,3(2H)-dione,
2-[[2-[[4-(2-pyridinyl)-1-piperazinyl]methyl]-cyclohexyl]methyl]hexahydro-4,7-methano-1H-isoindole-1,3(2H)-dione,
2-[[2-[[4-(2-pyridinyl)-1-piperazinyl]methyl]-cyclohexyl]methyl]hexahydro-1H-isoindole-1,3(2H)-dione,
2-[[2-[[4-(2-pyrimidinyl)-1-piperazinyl]methyl]-cyclohexyl]methyl]hexahydro-4,7-methano-1H-isoindole-1,3(2H)-dione,
2-[[2-[[4-(2-pyrimidinyl)-1-piperazinyl]methyl]-cyclohexyl]methyl]hexahydro-1H-isoindole-1,3(2H)-dione,
2-[[2-[[4-(3-chlorophenyl)-1-piperazinyl]methyl]-cyclohexyl]methyl]hexahydro-4,7-methano-1H-isoindole-1,3(2H)-dione,
2-[[2-[[4-(3-chlorophenyl)-1-piperazinyl]methyl]-cyclohexyl]methyl]hexahydro-1H-isoindole-1,3(2H)-dione,
2-[[2-[[4-(5-benzofuranyl)-1-piperazinyl]methyl]-cyclohexyl]methyl]hexahydro-4,7-methano-1H-isoindole-1,3(2H)-dione,
2-[[2-[[4-(5-benzofuranyl)-1-piperazinyl]methyl]-cyclohexyl]methyl]hexahydro-1H-isoindole-1,3(2H)-dione,
2-[[2-[[4-(1-naphthyl)-1-piperazinyl]methyl]-cyclohexyl]methyl]hexahydro-4,7-methano-1H-isoindole-1,3(2H)-dione,
2-[[2-[[4-(1-naphthyl)-1-piperazinyl]methyl]-cyclohexyl]methyl]hexahydro-1H-isoindole-1,3(2H)-dione,
2-[[2-[[4-[bis(4-fluorophenyl)methylene]-1-piperidyl]methyl]cyclohexyl]methyl]hexahydro-4,7-methano-1H-isoindole-1,3(2H)-dione,
2-[[2-[[4-[bis(4-fluorophenyl)methylene]-1-piperidyl]methyl]cyclohexyl]methyl]hexahydro-1H-isoindole-1,3(2H)-dione,
2-[[2-[[4-(2-methoxyphenyl)-1-piperazinyl]methyl]-cyclohexyl]methyl]hexahydro-4,7-methano-1H-isoindole-1,3(2H)-dione,
2-[[2-[[4-(2-methoxyphenyl)-1-piperazinyl]methyl]-cyclohexyl]methyl]hexahydro-1H-isoindole-1,3(2H)-dione,
2-[[2-[[4-(3-isoquinolyl)-1-piperazinyl]methyl]-cyclohexyl]methyl]hexahydro-4,7-methano-1H-isoindole-1,3(2H)-dione,
2-[[2-[[4-(3-isoquinolyl)-1-piperazinyl]methyl]-cyclohexyl]methyl]hexahydro-1H-isoindole-1,3(2H)-dione,
2-[[2-[[4-(8-quinolyl)-1-piperazinyl]methyl]cyclohexyl]methyl]hexahydro-4,7-methano-1H-isoindole-1,3(2H)-dione,
2-[[2-[[4-(8-quinolyl)-1-piperazinyl]methyl]-cyclohexyl]methyl]hexahydro-1H-isoindole-1,3(2H)-dione,
2-[[2-[[4-(1,2-benzisothiazol-3-yl)-1-piperazinyl]-methyl]cyclopentyl]methyl]hexahydro-4,7-methano-1H-isoindole-1,3(2H)-dione,
2-[[2-[[4-(1,2-benzisothiazol-3-yl)-1-piperazinyl]-methyl]cyclopentyl]methyl]hexahydro-1H-isoindole-1,3(2H)-dione,
2-[[3-[[4-(1,2-benzisothiazol-3-yl)-1-piperazinyl]-methyl]bicyclo[2.2.1]hept-2-yl]methyl]hexahydro-4,7-methano-1H-isoindole-1,3(2H)-dione,
2-[[3-[[4-(1,2-benzisothiazol-3-yl)-1-piperazinyl]-methyl]bicyclo[2.2.1]hept-2-yl]methyl]hexahydro-1H-isoindole-1,3(2H)-dione,
2-[[2-[[4-(7-benzofuranyl)-1-piperazinyl]methyl]-cyclohexyl]methyl]hexahydro-4,7-methano-1H-isoindole-1,3(2H)-dione,
2-[[2-[[4-(7-benzofuranyl)-1-piperazinyl]methyl]-cyclohexyl]methyl]hexahydro-1H-isoindole-1,3(2H)-dione,
2-[[3-[[4-(1,2-benzisothiazol-3-yl)-1-piperazinyl]-methyl]-7-oxabicyclo[2.2.1]hept-5-ene-2-yl]methyl]-hexahydro-4,7-methano-1H-isoindole-1,3(2M-dione,
2-[[3-[[4-(1,2-benzisothiazol-3-yl)-1-piperazinyl]-methyl]-7-oxabicyclo[2.2.1]hept-5-ene-2-yl]methyl]-hexahydro-1H-isoindole-1,3(2H)-dione,
2-[[6-[[4-(1,2-benzisothiazol-3-yl)-1-piperazinyl]-methyl]-3-cyclohexen-1-yl]methyl]hexahydro-4,7-methano-1H-isoindole-1,3(2H)-dione, and
2-[[6-[[4-(1,2-benzisothiazol-3-yl)-1-piperazinyl]-methyl]-3-cyclohexen-1-yl]methyl]hexahydro-1H-isoindole-1,3(2H)-dione.

In case that the optically active compound (7) and/or the optically active quaternary ammonium salt (4) are used in the reaction, the optically active corresponding imide compound (8) can be obtained.

In addition, the present invention includes the following process:

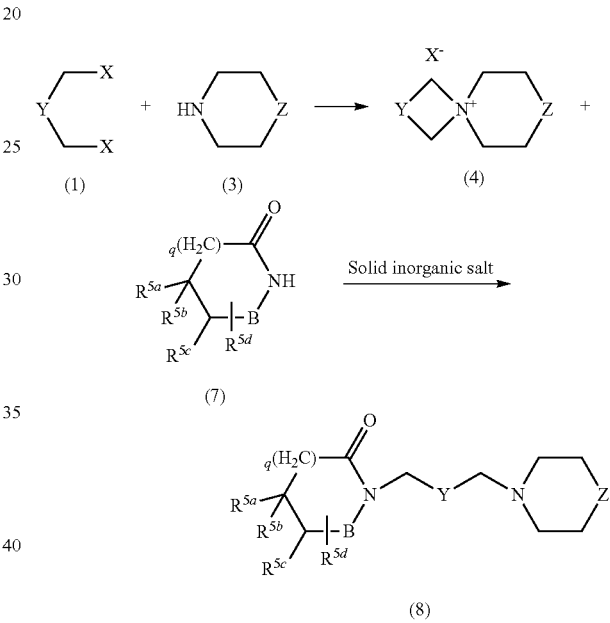

wherein the symbols described in the scheme are as defined in Terms 1 and 17 mentioned above.

EXAMPLE

Hereinafter, the present invention is illustrated in more detail by the following Example and Comparative Example, but it should not be construed to be limited thereto. The analyses in the examples were done by high-performance liquid chromatography (LC) or gas chromatography.

Example 1

A mixed solution of 4-(1,2-benzisothiazol-3-yl)piperazine [Compound (A)] (20.0 g, 91.2 mmol), (1R,2R)-1,2-bis(methanesulfonyloxymethyl)cyclohexane [Compound (B)] (13.7 g, 45.6 mmol), and toluene (140 g) was stirred under reflux for 3 hours to give a reaction mixture containing 4'-(1,2-benzisothiazol-3-yl)-(3aR,7aR)-octahydro-spiro[2H-isoindole-2,1'-piperazinium]methanesulfonate [Compound (C)]. And, the production rate of by-product (R) was 0.025% (which was calculated with the following formula (a)).

$$\text{Production rate of by-product derived from carbonate} = \quad (a)$$

$$\frac{\text{Total } LC \text{ area of by-product derived from carbonate}}{\text{Total } LC \text{ area of detected peaks except solvent}} \times 100$$

Example 2

To the reaction mixture containing Compound (C) which was obtained in the above Example 1 were added tetra-n-butyl ammonium hydrogen sulfate (0.62 g, 1.83 mmol), (3aR,4S,7R,7aS)-hexahydro-4,7-methano-2H-isoindole-1,3-dione [Compound (D)] (11.3 g, 68.4 mmol), potassium carbonate (7.6 g, 55.0 mmol) and water (0.4 g), and the resulting mixture was reacted under reflux for 3 hours. Then, the reaction mixture was cooled to room temperature, and water (200 g) was added to the mixture. The mixture was separated with a separating funnel, and the toluene layer was washed with 2.3% (W/W) brine (175 g). Further, active carbon (0.9 g) was added to the toluene solution, and the mixture was stirred for 1 hour. The active carbon was removed by filtration to give a toluene solution containing (3aR,4S,7R,7aS)-2-{(1R,2R)-2-[4-(1,2-benzisothiazol-3-yl)-piperazin-1-ylmethyl]cyclohexylmethyl}-hexahydro-4,7-methano-2H-isoindole-1,3-dione (2-[[(1R,2R)-2-[[4-(1,2-benzisothiazol-3-yl)-1-piperazinyl]methyl]-cyclohexyl]methyl]hexahydro-(3aS,4R,7S,7aR)-4,7-methano-1H-isoindole-1,3(2H)-dione) [Compound (E)] (266.5 g). The yield of Compound E was 94.3%. The yield of Compound (E) was calculated based on the analytical result that the content of the compound in the toluene solution was 7.9% (w/w) (which was calculated by LC absolute calibration curve method). And, the production rate of by-product (R) was 0.12% (which was calculated with the above formula (a)).

Example 3

To a mixture of Compound (A) (6.0 g, 27.4 mmol), Compound (B) (9.9 g, 33.0 mmol) and toluene (84 g) was added potassium carbonate (2.3 g, 16.6 mmol), and the mixture was reflux-dehydrated for 4 hours. After cooling the reaction mixture to 70° C. or lower, toluene (196 g), Compound (A) (34.0 g, 155.0 mmol) and Compound (B) (17.5 g, 58.3 mmol) were added to the reaction mixture, and then the reaction mixture was reflux-dehydrated again for 9 hours to give the reaction mixture containing Compound (C). The remained amount of Compound (B) in the supernatant toluene was 2.4% (which was calculated by GC absolute calibration curve method) (transformation rate: 97.6%). And, the production rate of by-product (R) was 0.31% which was analyzed by LC analysis and calculated with the above formula (a).

Example 4

To the reaction mixture containing Compound (C) which was obtained in the above Example 3 were added toluene (44.0 g), Compound (D) (16.6 g, 100.5 mmol) and potassium carbonate (25.2 g, 182.3 mmol), and then the toluene (44 g) was removed by heating. Then, the reaction mixture was cooled to 70° C. or lower, and water (0.8 g) was added to the mixture. The mixture was refluxed for 3 hours and it was checked that the production rate of by-product (6) was 0.10% (which was calculated with the following formula (b)).

$$\text{Production rate of by-product (6)}(\%) = \quad (b)$$

$$\frac{LC \text{ area of by-product (6)}}{LC \text{ area of by-product (6)} + \left\{ \begin{array}{l} (3aR, 4S, 7R, 7aS) - 2 - \\ (1R, 2R) - 2 - \\ \left[ 4 - \left( \begin{array}{c} 1, 2 - benzisothiazol - \\ 3 - + yl \end{array} \right) \right] - \\ piperazin - 1 - ylmethyl \\ cyclohexylmethyl \end{array} \right\} }$$
$$hexahydro - 4, 7 - methano - 2H -$$
$$isoindole - 1, 3 - dione$$

The reaction mixture was cooled, and water (400.0 g) was added to the mixture. The mixture was separated with a separating funnel, and the toluene layer was washed with 0.8% hydrochloric acid (400 g), and then 2.3, % (w/w) brine (350 g). Further, active carbon (1.8 g) was added to the toluene solution, and the mixture was stirred for 1 hour. The active carbon was removed by filtration and washed with toluene to give a toluene solution containing Compound (E) (385.1 g). The yield of Compound E was 93.4%. The yield of Compound (E) was calculated based on the analytical result that the content of the compound in the toluene solution was 10.9% (w/w) (which was calculated by LC absolute calibration curve method). And, the production rate of by-product (R) was 1.21% (which was calculated with the above formula (a)).

Example 5

To a mixture of Compound (A) (6.0 g, 27.4 mmol), Compound (B) (9.9 g, 33.0 mmol) and toluene (84 g) was added potassium carbonate (2.3 g, 16.6 mmol), and the resulting mixture was reflux-dehydrated for 4 hours. After cooling the reaction mixture to 70° C. or lower, toluene (196 g), Compound (A) (94.0 g, 428.6 mmol) and Compound (B) (17.5 g, 58.3 mmol) were added to the reaction mixture, and then the reaction mixture was reflux-dehydrated again for 4 hours to give the reaction mixture containing Compound (C). The remained amount of Compound (B) in the supernatant toluene was less than the detection limit of GC (transformation rate: 100%). And, the production rate of by-product (R) was 0.09% which was analyzed by LC analysis and calculated with the above formula (a).

Example 6

To the reaction mixture containing Compound (C) which was obtained in the above Example 5 were added toluene (44.0 g), Compound (D) (16.6 g, 100.5 mmol) and potassium carbonate (25.2 g, 182.3 mmol), and then the toluene (44 g) was removed by heating. Then, the reaction mixture was cooled to 70° C. or lower, and water (0.8 g) was added to the mixture. The mixture was refluxed for 2 hours and it was checked that the production rate of by-product (6) was 0.10% (which was calculated with the above formula (b)). The reaction mixture was cooled, and water (400.0 g) was added to the mixture. The mixture was separated with a separating funnel, and the toluene layer was washed with 1.6% hydrochloric acid (800 g), and then 2.3% (w/w) brine (350 g). Further, active carbon (1.8 g) was added to the toluene solution, and the mixture was stirred for 1 hour. The active carbon was removed by filtration and washed with toluene to give a toluene solution containing Compound (E) (385.1 g). The yield of Compound (E) was 91.5%. The yield of Compound (E) was calculated based on the analytical result that the content of the compound in the toluene solution was 10.4% (w/w) (which was calculated by LC absolute calibration curve method). And, the production rate of by-product (R) was 1.85% (which was calculated with the above formula (a)).

Example 7

To a mixture of Compound (A) (6.0 g, 27.4 mmol), Compound (B) (9.9 g, 33.0 mmol) and toluene (97 g) was added potassium carbonate (2.3 g, 16.6 mmol), the toluene (13.4 g) was removed by heating, and then the mixture was reflux-dehydrated for 4 hours. After cooling the reaction mixture to 70° C. or lower, toluene (227 g), Compound (A) (30.0 g, 136.8 mmol) and Compound (B) (17.5 g, 58.3 mmol) were added to the reaction mixture, the toluene (30.6 g) was removed, and then the reaction mixture was reflux-dehydrated again for 20 hours to give the reaction mixture containing Compound (C). The remained amount of Compound (B) in the supernatant toluene was 1.4% (transformation rate: 98.6%). And, the production rate of by-product (R) was 1.28% which was analyzed by LC analysis and calculated with the above formula (a).

Example 8

To the reaction mixture containing Compound (C) which was obtained in the above Example 7 were added toluene (44.0 g), Compound (D) (16.6 g, 100.5 mmol) and potassium carbonate (22.7 g, 164.2 mmol), and then the toluene (44 g) was removed by heating. Then, the reaction mixture was cooled to 70° C. or lower, and water (0.8 g) was added to the mixture. The mixture was refluxed for 4.5 hours. The reaction mixture was cooled, and water (400.0 g) was added to the mixture. The mixture was separated with a separating funnel, and the toluene layer was washed with 3.6% hydrochloric acid (313 g), and then 2.3% (w/w) brine (350 g). Further, active carbon (1.8 g) was added to the toluene solution, and the mixture was stirred for 1 hour. The active carbon was removed by filtration and washed with toluene to give a toluene solution containing Compound (E) (413.3 g). The yield of Compound (E) was 85.6%. The yield of Compound (E) was calculated based on the analytical result that the content of the compound in the toluene solution was 9.3% (w/w) (which was calculated by LC absolute calibration curve method). And, the production rate of by-product (R) was 1.44% (which was calculated with the above formula (a)).

Comparative Example 1

To a mixture of Compound (A) (140.1 kg, 638.8 mol), Compound (B) (230.3 kg, 766.7 mol) and toluene (2272 kg) was added potassium carbonate (53.0 kg, 383.5 mol), the toluene (312 kg) was removed by heating, and then the mixture was reflux-dehydrated for 5 hours. Then, the reaction mixture was cooled to 70° C. or lower, and potassium carbonate (26.5 kg, 191.7 mol) and tetra-n-butyl ammonium hydrogen sulfate (8.7 kg, 25.6 mol) were added to the mixture. The mixture was refluxed for 10 hours to give the reaction mixture containing Compound (C).

Comparative Example 2

To the reaction mixture containing Compound (C) which was obtained in the above Comparative Example 1 were added toluene (309.6 kg), Compound (D) (158.3 kg, 958.3 mol) and potassium carbonate (105.9 kg, 766.2 mol), and then the toluene (308 kg) was removed by heating. Then, the reaction mixture was cooled to 70° C. or lower, and water (5.7 kg) was added to the mixture. The mixture was refluxed for 4 hours. The reaction mixture was cooled, and water (2819 kg) was added to the mixture. The mixture was separated with a separating funnel, and the toluene layer was washed with 2.3% (w/w) brine (2466 kg). Further, active carbon (12.5 kg) was added to the toluene solution, and the mixture was stirred for 1 hour. The active carbon was removed by filtration and washed with toluene to give a toluene solution containing Compound (E) (2562 kg). The yield of Compound (E) was 87.7% The yield of Compound (E) was calculated based on the analytical result that the content of the compound in the toluene solution was 10.8% (w/w) (which was calculated by LC absolute calibration curve method). And, the production rate of by-product (R) was 9.83% (which was calculated with the above formula (a)).

Comparative Example 3

To a mixture of Compound (A) (90.0 kg, 410.4 mol), Compound (B) (147.9 kg, 492.4 mol) and toluene (1460 kg) were added potassium carbonate (34.0 kg, 246.0 mol) and water (636 g), the toluene (298 kg) was removed by heating, and then the mixture was reflux-dehydrated for 34 hours. Then, the reaction mixture was cooled to 70° C. or lower, and potassium carbonate (17.0 kg, 123.0 mol) and tetra-n-butyl ammonium hydrogen sulfate (5.6 kg, 16.5 mol) were added to the mixture. The mixture was refluxed for 12 hours to give the reaction mixture containing Compound (C). And, the production rate of by-product (R) was 3.02% (which was calculated with the above formula (a)).

Comparative Example 4

To the reaction mixture containing Compound (C) which was obtained in the above Comparative Example 3 were added toluene (198 kg), Compound (D) (101.7 kg, 615.7 mol) and potassium carbonate (68.1 kg, 492.7 mol), and then the toluene (198 kg) was removed by heating. Then, the reaction mixture was cooled to 70° C. or lower, and water (3.7 kg) was added to the mixture. The mixture was refluxed for 3 hours. The reaction mixture was cooled, and water (1803 kg) was added to the mixture. The mixture was separated with a separating funnel, and the toluene layer was washed with 2.3% (w/w) brine (1578 kg). Further, active carbon (8.0 kg) was added to the toluene solution, and the mixture was stirred for 1 hour. The active carbon was removed by filtration and washed with toluene to give a toluene solution containing Compound (E) (1625 kg). The yield of Compound (E) was 90.1%. The yield of Compound (E) was calculated based on the analytical result that the content of the compound in the toluene solution was 11.2% (w/w) (which was calculated by LC absolute calibration curve method). And, the production rate of by-product (R) was 3.08% (which was calculated with the above formula (a)).

Each reaction time, product yield, and by-product yield in the above examples and comparative examples is shown in the following table.

| | Process | Compound (A) (mol) | Inorganic salt (mol) | Reaction time (hr) | Product yield (%) | By-product (R) (%) | By-product (6) (%) |
|---|---|---|---|---|---|---|---|
| Example 1 | (A) | 2.0 | — | 3 | | 0.025 | |
| Example 2 | (B) | | 1.2 | | 94 | 0.12 | — |
| Example 3 | (A) | 2.0 | 0.18 | 13 | | 0.31 | |
| Example 4 | (B) | | 2.0 | | 93 | 1.21 | 0.10 |
| Example 5 | (A) | 5.0 | 0.18 | 8 | | 0.09 | |
| Example 6 | (B) | | 2.0 | | 92 | 1.85 | 0.10 |
| Example 7 | (A) | 1.8 | 0.18 | 24 | | 1.28 | |
| Example 8 | (B) | | 1.8 | | 86 | 1.44 | — |
| Comparative Example 1 | (A) | 0.83 | 0.75 | 15 | | — | |
| Comparative Example 2 | (B) | | 1.0 | | 88 | 9.83 | — |
| Comparative Example 3 | (A) | 0.83 | 0.75 | 46 | | 3.02 | |
| Comparative Example 4 | (B) | | 1.0 | | 90 | 3.08 | — |

Process (A): Compound (A) + Compound (B) --> quaternary ammonium salt (C)
Process (B): quaternary ammonium salt (C) + Compound (D) --> imide compound (E)

According to the results of Examples 1, 3, 5 and 7, the process of the present invention can make the reaction time for preparing quaternary ammonium salt (4) shortened, i.e. the reaction times in all the examples could be steadily shortened in 24 hours. In addition, the transformation rate to Compound (1) in the reaction has been enhanced by the present invention. In particular, the transformation rates in Example 3, 5 and 7 are about 100%, thus it is thought that the present invention has industrially excellent merits. Thereby, imide compound (8) could be also prepared in high yield in 2 steps via quaternary ammonium salt (4). Furthermore, the production of by-product (R) could be drastically held down by the present invention. Accordingly, the process of the present invention is an industrially useful manufacturing method which is also for practical preparation.

Industrial Applicability

The process of the present invention is a process for preparing quaternary ammonium salt (4) in steady reaction time and in steady quality, thus it has some merits, in particular for the industrial purpose.

The invention claimed is:
1. A process for preparing a quaternary ammonium salt of formula (4):

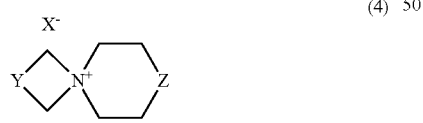

(4)

wherein
X is halogen atom, $C_{1-6}$ alkylsulfonyloxy group, or $C_{6-10}$ arylsulfonyloxy group, and $X^-$ is a counteranion thereof,
Y is a substituent of the following formula (2a) or (2b):

(2a)

(2b)

wherein $R^1$ is independently methylene or oxygen atom; $R^2$ is independently $C_{1-6}$ alkyl group, $C_{1-6}$ alkoxy group, or hydroxy group; m and n are independently 0, 1, 2, or 3; and p is 1 or 2, and
Z is =N—$R^3$ or =CH—$R^4$ wherein $R^3$ is $C_{1-6}$ alkyl group, $C_{3-7}$ cycloalkyl group, $C_{5-7}$ cycloalkenyl group, $C_{6-10}$ aryl group, or 5- to 10-membered monocyclic or bicyclic heteroaryl group; $R^4$ is $C_{1-6}$ alkyl group, $C_{1-6}$ alkoxy group, $C_{1-6}$ alkylthio group, $C_{3-7}$ cycloalkyl group, $C_{3-7}$ cycloalkyloxy group, $C_{3-7}$ cycloalkylthio group, $C_{5-7}$ cycloalkenyl group, $C_{5-7}$ cycloalkenyloxy group, $C_{5-7}$ cycloalkenylthio group, $C_{6-10}$ aryl group, $C_{6-10}$ aryloxy group, $C_{6-10}$ arylthio group, 5- to 10-membered monocyclic or bicyclic heteroaryl group, 5- to 10-membered monocyclic or bicyclic heteroaryloxy group, or 5- to 10-membered monocyclic or bicyclic heteroarylthio group,
comprising reacting a compound of formula (1):

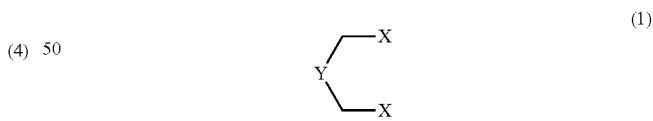

(1)

wherein X is independently selected from the above-defined ones, and Y is as defined above,
with 1.8 to 15 mole of a compound of formula (3):

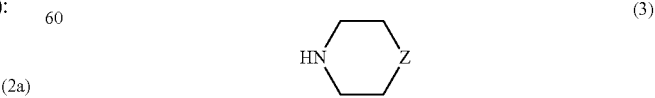

(3)

wherein Z is as defined above, per one mole of the compound of formula (1) to prepare the quaternary ammonium salt of formula (4).

2. The process of claim 1 wherein the reaction of Compound (1) with Compound (3) includes the following steps (i) and (ii):
   step (i): reacting Compound (1) with 0.1 to 1.0 mole of Compound (3) per one mole of Compound (1), and then
   step (ii): adding the rest of Compound (3) to the reaction mixture so that the total amount of Compound (3) can be 1.8 to 15 mole per one mole of Compound (1), and continuing the reaction.

3. The process of claim 1 wherein the reaction of Compound (1) with Compound (3) includes the following steps (i) and (ii):
   step (i): reacting 0.1 to 1.0 mole of Compound (1) with 0.1 to 1.0 mole of Compound (3) per one mole of the total amount of Compound (1), and then
   step (ii): adding the rest of Compound (1) and the rest of Compound (3) to the reaction mixture so that the total amount of Compound (3) can be 1.8 to 15 mole per one mole of the total amount of Compound (1), and continuing the reaction.

4. The process of claim 2 wherein the reaction is carried out in the presence of 0.1 to 1.0 mole of solid inorganic base per one mole of the total amount of Compound (1).

5. The process of claim 4 wherein the solid inorganic base is potassium carbonate.

6. The process of claim 4 wherein the amount of an solid inorganic base is 0.1 to 0.3 mole per one mole of the total amount of Compound (1).

7. The process of claim 2 wherein the amount of Compound (3) added in step (i) is 0.1 to 0.5 mole per one mole of the total amount of Compound (1).

8. The process of claim 2 wherein the total amount of Compound (3) in step (ii) is 1.8 to 5 mole per one mole of Compound (1).

9. The process of claim 1 wherein X is independently $C_{1-6}$ alkylsulfonyloxy group, or $C_{6-10}$ arylsulfonyloxy group.

10. The process of claim 9 wherein X is methanesulfonyloxy group.

11. The process of claim 1 wherein Y is the substituent of formula (2a).

12. The process of claim 11 wherein m is 2 and n is 0.

13. The process of claim 1 wherein Z is $=N-R^3$.

14. The process of claim 13 wherein $R^3$ is 5- to 10-membered monocyclic or bicyclic heteroaryl group.

15. The process of claim 14 wherein $R^3$ is 1,2-benzisothiazol-3-yl.

16. A process for preparing a quaternary ammonium salt of formula (4a):

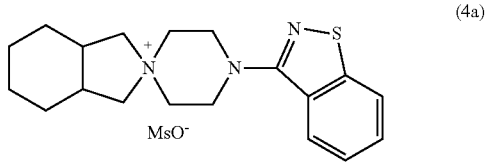

(4a)

comprising reacting a compound of formula (1a):

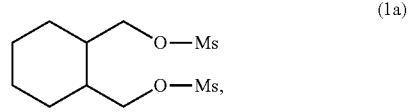 [SMILES: CS(=O)(=O)OCC1CCCCC1COS(C)(=O)=O]

(1a)

with 1.8 to 15 mole of a compound of formula (3a):

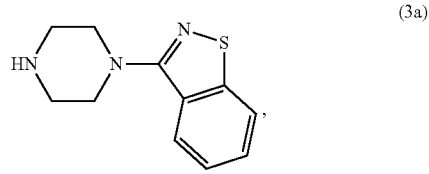 [SMILES: c1ccc2c(N3CCNCC3)nsc2c1]

(3a)

per one mole of the compound of formula (1a) to prepare the quaternary ammonium salt of formula (4a).

17. The process of claim 16 wherein the compound of formula (1a) is

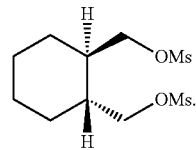 [SMILES: CS(=O)(=O)OC[C@@H]1CCCC[C@H]1COS(C)(=O)=O]

* * * * *